US008197620B2

(12) United States Patent
Spyckerelle et al.

(10) Patent No.: US 8,197,620 B2
(45) Date of Patent: Jun. 12, 2012

(54) METHOD FOR DETERMINING THE SENSITIVE OR INSENSITIVE NATURE OF A HEXOGEN

(75) Inventors: Christian Spyckerelle, Jonquerettes (FR); Geneviéve Eck, Monteux (FR); Jean Guillaumin, Bedarrides (FR)

(73) Assignee: Eurenco, Paris (FR)

( * ) Notice: Subject to any disclaimer, the term of this patent is extended or adjusted under 35 U.S.C. 154(b) by 112 days.

(21) Appl. No.: 12/663,122

(22) PCT Filed: Jun. 5, 2008

(86) PCT No.: PCT/FR2008/051005
§ 371 (c)(1), (2), (4) Date: May 26, 2010

(87) PCT Pub. No.: WO2009/001006
PCT Pub. Date: Dec. 31, 2008

(65) Prior Publication Data
US 2010/0258223 A1    Oct. 14, 2010

(30) Foreign Application Priority Data
Jun. 6, 2007 (FR) ..................... 07 55501

(51) Int. Cl.
*C06B 25/00* (2006.01)
*C06B 25/34* (2006.01)
*D03D 23/00* (2006.01)
*D03D 43/00* (2006.01)

(52) U.S. Cl. ...... 149/92; 149/88; 149/108.8; 149/109.2; 149/109.4; 149/109.6

(58) Field of Classification Search ............ 149/92, 149/88, 108.8, 109.2, 109.4, 109.6
See application file for complete search history.

(56) References Cited

U.S. PATENT DOCUMENTS

| | | | |
|---|---|---|---|
| 3,455,749 A * | 7/1969 | Gow | 149/4 |
| 5,059,261 A * | 10/1991 | Condo et al. | 149/19.92 |
| 5,529,649 A * | 6/1996 | Lund et al. | 149/19.3 |
| 5,587,553 A * | 12/1996 | Braithwaite et al. | 149/19.6 |
| 6,736,913 B1 * | 5/2004 | Hatch | 149/19.92 |

(Continued)

FOREIGN PATENT DOCUMENTS
WO   WO 2004/027386 A2   4/2004

OTHER PUBLICATIONS

Lochert, I. et al. "Reduced Sensitivity RDX (RS-RDX) Part 1: Literature Review and DSTO Evaluation" DSTO Systems Sciences Laboratory, Jul. 2003, XP007904014.

(Continued)

*Primary Examiner* — James McDonough
(74) *Attorney, Agent, or Firm* — Hamre, Schumann, Mueller & Larson, P.C.

(57) ABSTRACT

The present invention relates to a process for determining the sensitive or insensitive nature of a crystalline hexogen. Said process comprises:
  the formulation of said crystalline hexogen in a matrix;
  the analysis of a sample of said matrix charged with said crystalline hexogen by differential scanning calorimetry;
  said matrix consisting essentially of at least one liquid polymer that is suitable for the formulation of binders for energetic materials charged with nitro organic explosives; and
    of at least one adsorbent for the volatile organic compounds, which is stable at the operating temperature of the analysis and which has low affinity for water.
The present invention also relates to the crystalline hexogen in such a matrix.

18 Claims, 1 Drawing Sheet

U.S. PATENT DOCUMENTS

| | | | | |
|---|---|---|---|---|
| 6,932,878 | B1 * | 8/2005 | Hallam et al. | 149/19.91 |
| 6,984,275 | B1 * | 1/2006 | Walsh et al. | 149/19.7 |
| 7,328,643 | B2 * | 2/2008 | Goetsch et al. | 86/50 |
| 7,694,628 | B2 * | 4/2010 | Adebimpe et al. | 102/355 |

OTHER PUBLICATIONS

Freche, A. et al. "Insensitive RDX (1-RDX)", Insensitive Munitions and Energetic Materials Technology Symposium—Technology Implementation in the 21$^{st}$ Century, San Antonio, Texas, 2000, pp. 1-5.

Freche, M. A. et al. "Insensitive Nitramines", Insensitive Munitions and Energetic Materials Technology Symposium, Orlando, FL, 2003.

Lecume, S. et al. Two RDX Qualities for PBXN-109 Formulation Sensitivity Comparison, Insensitive Munitions and Energetic Materials Symposium, Bordeaux, 2001.

Eriksen, J., STANAG 4488 PCS (Edition 1)—Explosives, Shock Sensitivity Tests, fourth revised edition, ST/SG/AC.10/11/Rev.4, ISBN 92-1-239083-8ISSN 1014-7179, Sep. 2001.

van Wijk, R. "High-Temperature (over 400° C) Resistant Polymeric Column Packing Material", Chimia, vol. 24, 1970, pp. 254-256.

van Wijk, R. "The Use of Poly-Para-2, 6-Diphenyl-Phenylene Oxide as a Porous Polymer in Gas Chromatography", Journal of Chromatographic Science, Jul. 1970, pp. 418-420.

* cited by examiner

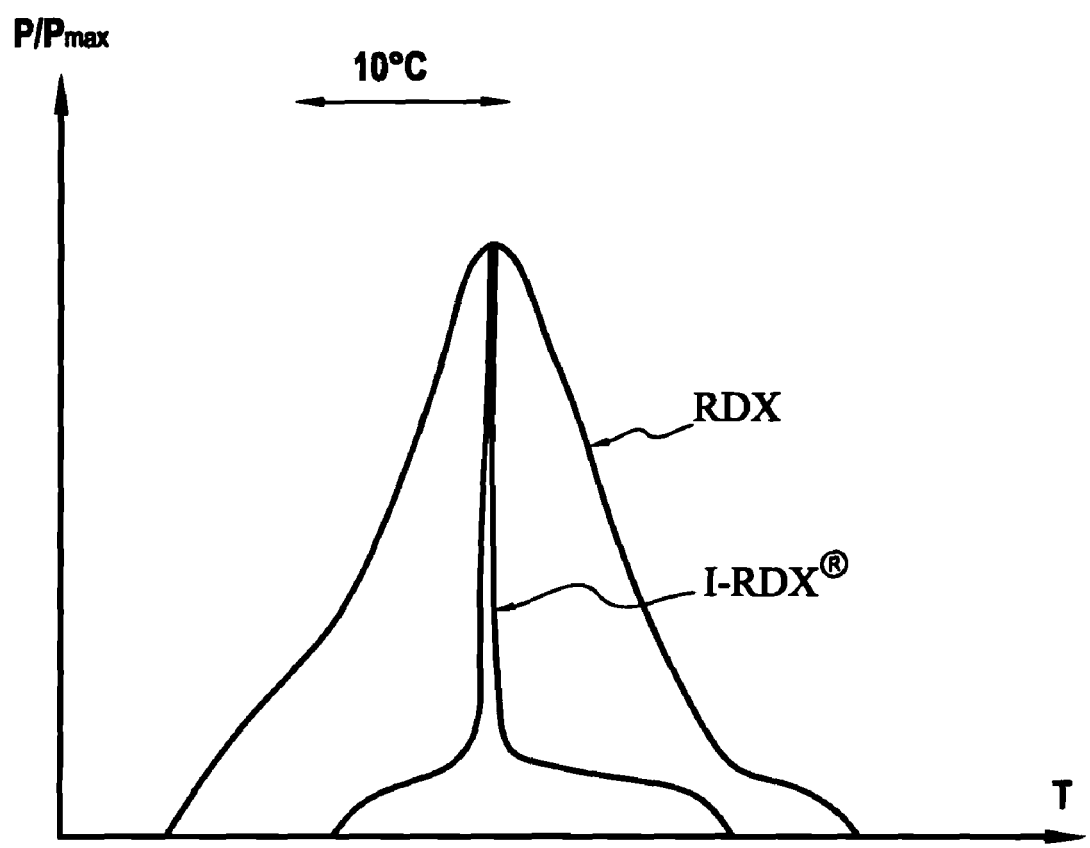

METHOD FOR DETERMINING THE SENSITIVE OR INSENSITIVE NATURE OF A HEXOGEN

The present invention relates mainly to a process for determining the sensitive or insensitive nature of a crystalline hexogen (hexogen=cyclotrimethylene trinitramine or RDX). The invention also relates to a novel formulation of crystalline hexogen, which is most particularly suitable for performing said process.

In other words, the present invention mainly proposes a novel method for differentiating a hexogen of standard grade from an "insensitive" hexogen. This method has many advantages over the differentiation methods known to date (DAI test and NQR and AFM methods presented later).

The explosive molecule hexogen (cyclotrimethylene trinitramine or RDX) has been, since its discovery during the Second World War, widely used for military applications. RDX (RDX-based compositions) is (are) especially found in explosive charges for munitions, in detonation relays, in civil demolition explosives, in composite explosives, in explosive cords, in charges formed for oil drilling, and in powder and solid propellants for weapons.

It is only in recent years that a grade of RDX of reduced sensitivity, known as I-RDX® (Insensitive-RDX) or RS-RDX (Reduced-Sensitivity RDX), has been described and produced in bulk; see especially in this respect:

Freche, A.; Aviles, J.; Donnio, L. and Spyckerelle, C., (2000), *Insensitive RDX (I-RDX), Insensitive Munitions and Energetic Materials Symposium—Technology Implementation in the 21st Century*, San Antonio, Tex.

Freche, A.; Spyckerelle, C. and Lecume, S., (2003), *SNPE insensitive Nitramines, Insensitive Munitions and Energetic Materials Technology Symposium*, Orlando, Fla.

This grade of RDX, available in the usual particle size ranges, is used in place of standard RDX in energy materials. This replacement allows better classification of the products with respect to their impact sensitivity, without modifying the other properties (for example the physical and chemical properties, the performance qualities, the fast and slow reaction to heating ("cook-offs"), to bullet impact, etc.). This was particularly confirmed with "cast" PBX compositions and solid propellants for self-propulsion.

Compositions, such as PBXN-109 composed of an RDX/Al/HTPB mixture (RDX/Aluminum/HydroxyTelechelic PolyButadiene mixture), prepared with this grade of hexogen have reduced sensitivity to shockwaves, measured by means of the DAI test (Detonation Aptitude Index, described in the text hereinbelow); see especially in this respect: Lecume, S.; Chabin, P. and Brunet P., (2001), *Two RDX Qualities for PBXN-109 Formulation Sensitivity Comparison, 2001, Insensitive Munitions and Energetic Materials Symposium*, Bordeaux.

The value of such a grade of hexogen is undeniable in the context of reducing the vulnerability of munitions.

Currently, "insensitive" hexogen that is in solid form cannot be differentiated physicochemically from standard hexogen. The "standard" physicochemical characterization techniques (examples that may be mentioned include: chromatographic techniques, granulometric characterizations, density determination) do not allow a qualitative or quantitative differentiation of "insensitive" hexogen from standard hexogen. Standard differential scanning calorimetry (DSC), as described in standard NF EN IS 11357-1, does not itself either make it possible to differentiate the two grades of hexogen, and the analysis of formulated explosive compositions based on RDX, such as PBXN-109, is not sufficiently discriminate to indicate the presence of the I-RDX® crystal.

Only sensitivity tests of the type such as "initiation of detonation through a barrier", also known as DAI (the Detonation Aptitude Index) on the formulated solid explosive object (see hereinbelow) containing the crystal may reveal the quality of the RDX used.

The DAI test is performed according to standard NFT 70-502 (see also UNO—Recommendations relating to the transportation of hazardous merchandise—manual of tests and criteria, fourth revised edition, ST/SG/AC.10/11/Rev.4, ISBN 92-1-239083-8ISSN 1014-7179 and STANAG 4488). It consists in determining the reactivity of an explosive substance subjected to detonation of a priming relay through a barrier composed of cellulose acetate boards. The limit thickness of the barrier for which there is no priming of the detonation of a second relay placed in contact with the other opposite the specimen is determined. This method was revealed early, in 1958, in U.S. Pat. No. 2,832,213.

Such a method is applicable to any type of solid, pasty or gelled explosive substance. Its extension to liquid explosives is especially described in U.S. Pat. No. 2,832,213.

U.S. Pat. Nos. 5,472,531, 5,316,600 and FR 2 667 592 give examples of safety results obtained on different types of explosive using said method (DAI test).

The DAI test applied directly to RDX crystals does not make it possible to distinguish the two grades of product. However, the result of the DAI test on a reference composition PBXN-109 leads, in the case of using I-RDX® to a number of boards of between 120 and 150, whereas this number is significantly higher and may exceed 200 in the case of a composition PBXN-109 using RDX crystal.

The DAI test may thus be conclusive, but it nevertheless intrinsically has a certain number of drawbacks. It involves:
  the preparation of the composition (the test not being performed directly on hexogen) and the production of the pyrotechnic objects,
  high cost,
  a large amount of material required to perform it, about 3 to 5 kg, all the more so since said test is destructive, and
  a duration of the characterization.

Furthermore, by its very nature, this test generates pyrotechnic effects and requires special test infrastructures.

A person skilled in the art is thus in search of a simple method for differentiating a hexogen of standard grade from an "insensitive" hexogen, which method would be free of the drawbacks of the DAI test.

With this aim, an international working group, led by the "Munition Safety Information Analysis Center" (MSIAC)" bureau of NATO, focuses on evaluating new potential methods for the characterization of RS-RDX (or I-RDX®).

Two newly developed methods enable this difference to be made. These are NQR (Nuclear Quadrupole Resonance) and AFM (Atomic Force Microscopy).

In an NQR spectrum, the line widths are directly proportional to the number of defects (in the broad sense) in the crystal lattice. The NQR analyses performed on seven hexogens show that the finer the peak, the more insensitive the hexogen. This technique has the advantage of being able to be performed directly on the hexogen sample and requires only 5 to 10 g of product. Its major drawback lies in the apparatus itself (high cost, and machine not available "off-the-shelf").

An AFM analysis provides data regarding the morphology, the defects (nature and number) and the roughness parameters of the crystals. On eight hexogens, it was possible to make a first correlation between the DAI result of the composition PBXN-109 and the number of defects at the surface of the crystal. This technique requires only a few mg of material. However, it is an expensive technique.

In such a context, the inventors now propose a novel method, which is simple to use, for differentiating a crystalline hexogen of standard grade (sensitive) from an "insensitive" crystalline hexogen. In other words, they propose a novel process, which is simple to use, for determining the sensitive or insensitive nature of crystalline hexogen. In characteristic terms, said method or said process comprises:

the formulation of said crystalline hexogen in a matrix;

the analysis of a sample of said matrix charged with said crystalline hexogen by differential scanning calorimetry;

said matrix consisting essentially of at least one liquid polymer that is suitable for the formulation of binders for energetic materials charged with nitro organic explosives; and of at least one adsorbent for volatile organic compounds, which is stable at the operating temperature of the analysis and which has low affinity for water.

In characteristic terms, said method or said process of the invention comprises a novel formulation of crystalline hexogen that enables the discrimination of the two grades of hexogen via differential scanning calorimetry (DSC). It has been seen, in the introduction to the present text, that said differential scanning calorimetry does not enable such a discrimination when it is used directly on the hexogens under consideration (pure hexogens).

The process of the invention thus combines a novel formulation of crystalline hexogen (it has been incorporated, by mixing, into a specific matrix) with a particular analysis technique (differential scanning calorimetry). The novelty of said invention in fact lies in the nature of the matrix within which the hexogen is mixed for analysis by differential scanning calorimetry.

Analysis of a material by differential scanning calorimetry is an analysis that is known per se, which is familiar to those skilled in the art. It consists in determining the enthalpies of thermal phenomena (such as changes of physical state or thermal reactions), by measuring the differential heat flow required to maintain the sample of material, on the one hand, and an inert reference, on the other hand, at the same temperature. This type of analysis is used, for example, to compare the temperatures at the maximum of the decomposition peaks of substances alone and of mixtures incorporating said substances.

This type of analysis, which is known per se, is thus, according to the invention, used in a characteristic manner on a sample containing crystalline hexogen (whose sensitive or insensitive nature it is desired to determine) in a matrix consisting essentially:

on the one hand, of at least one liquid polymer that is suitable for formulating binders for energetic materials charged with nitro organic explosives: this type of material is obviously compatible with hexogen (nitro organic explosives); it is conventionally used as prepolymer in the formulation of binders for composite explosives, and on the other hand, of at least one adsorbent for volatile organic compounds (VOC), which is stable at the operating temperature of the analysis (at least up to 230° C. or even beyond: 400° C. and more) and which has low affinity for water. Such VOC adsorbents, of the porous polymer type (having a high specific surface area), are notably commonly used as stationary phase in gas-phase chromatography columns.

Said matrix generally essentially consists of one such liquid polymer combined with one such adsorbent for volatile organic compounds. It is advantageously 100% formed from such a binary combination.

A person skilled in the art will already have appreciated the full value of the process of the invention. It offers many advantages, especially when compared with the DAI test and the two techniques (NQR and AFM) mentioned hereinabove:

said process is performed on hexogen itself (in a matrix, but not in an explosive composition (see the DAI test));

the analysis technique under consideration (DSC) is rapid and of low operating cost;

said analysis technique and the means for performing it are known;

said technique requires, for its implementation, only a small amount of product (about 50 mg of RDX).

It is now proposed to specify, without any implied limitation whatsoever, the implementation of the process of the invention, the implementation of each of the two successive steps of formulation and analysis of said process of the invention.

As regards the formulation (by simple mixing) of crystalline hexogen (whose sensitive or insensitive nature it is desired to know) in a matrix, the following may be indicated.

The crystalline hexogen is generally introduced into said matrix (by mixing) in amounts such that the charged matrix contains from 35% to 65% by mass of said hexogen.

In general, said charged matrix (to be analyzed by DSC in the context of the process of the invention) contains:

from 35% to 65% by mass of said crystalline hexogen, from 25% to 50% by mass of said at least one liquid polymer, and from 5% to 20% by mass of said at least one adsorbent.

Advantageously, said charged matrix contains:

from 46% to 59% by mass of said crystalline hexogen, from 31% to 43% by mass of said at least one liquid polymer, and from 8% to 14% by mass of said at least one adsorbent.

Said at least one liquid polymer is advantageously chosen from polyethylene glycols, polyoxypropylene glycols, polyesters and polyethers with hydroxyl end groups. A person skilled in the art knows these crosslinkable inert prepolymers, used especially in the formulation of propellants (containing nitro organic explosives). Said polyethylene glycols, polyoxypropylene glycols, polyesters and polyethers containing hydroxyl end groups advantageously have a molecular mass of between 1500 and 5000 g/mol.

Said at least one liquid polymer may also advantageously consist of a hydroxytelechelic polybutadiene (I-ITPB). This type of compound is also widely used in the formulation of binders for energetic materials charged with nitro organic explosives. For the use for the purposes of the invention, it generally has a molecular mass of between 500 and 10 000 g/mol and advantageously a molecular mass of between 2000 and 3000 g/mol.

Said at least one liquid polymer, the first constituent element of the hexogen formulation matrix for the purposes of performing the analysis by DSC, thus very advantageously consists of one of the polymers identified above.

Said at least one adsorbent for volatile organic compounds is advantageously a porous polymer based on a polyphenylene oxide containing 2,6-diphenyl-p-phenylene oxide units. Said polyphenylene oxide (RN 24938-68-9) corresponds to the formula below:

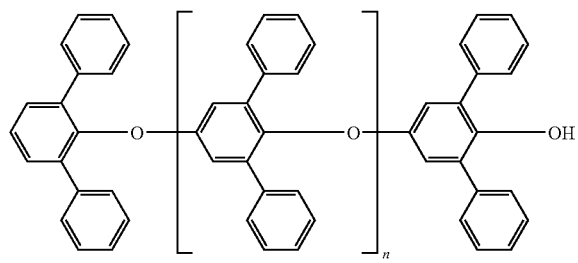

It advantageously has a high molecular mass, of between 0.5 and $1\times10^6$ g/mol (which corresponds to values of n generally of between 2000 and 4000).

The use (for purposes other than those of the invention: gas-phase chromatography) of this type of adsorbent has especially been described in U.S. Pat. No. 4,003,257. Additional descriptions of the polymer under consideration are given in Chimia, Vol. 24, pp. 254-56, 1970: "High Temperature (over 400° C.) Resistant Polymeric Column Packing Material" by R. van Wijk and in Journal of Chromatographic Science, July, 1970, pp. 418-420: "The Use of Poly-para-2, 6-diphenylphenylene Oxide as a Porous Polymer in Gas Chromatography" by R. van Wijk.

This type of adsorbent is notably commercially available under the name Tenax®. There are in fact different forms of Tenax®: Tenax®-GC, Tenax®-GR, Tenax®-TA, etc. sold by the companies Aldrich, Supelco and Buchem B.V. Insofar as it has low affinity for water, Tenax®-TA is particularly efficient at trapping volatile and semivolatile organic compounds, present in aqueous samples. Tenax®-TA is particularly recommended as an adsorbent for the hexogen formulation matrix, in the context of performing the process of the invention.

Other adsorbents for volatile organic compounds may be suitable for use. They should obviously satisfy the specifications listed hereinabove:
  be adsorbents for volatile compounds,
  be stable at the operating temperature of the analysis (DSC); and
  have low affinity for water.

According to one particularly advantageous implementation variant, the determination process of the invention involves the formulation of hexogen (whose sensitive or insensitive nature it is desired to determine) in a matrix consisting essentially:
  of a hydroxytelechelic polybutadiene, with a molecular mass of between 2000 and 3000 g/mol; and
  of a porous polymer based on a polyphenylene oxide containing 2,6-diphenyl-p-phenylene oxide units, with a molecular mass of between 0.5 and $1\times10^6$ g/mol.

As regards the analysis to be performed, in the context of the process of the invention, it is thus a DSC analysis of a sample of the matrix, as described above, charged with crystalline hexogen (whose sensitive or insensitive nature it is desired to determine).

Conventionally, to perform such an analysis (by DSC), a few $mm^3$ of sample are used.

Entirely surprisingly, the analysis by DSC of such a sample (of said specific matrix charged with crystalline hexogen) makes it possible to identify the exact nature of the hexogen under consideration (sensitive (standard) hexogen or insensitive hexogen). The inventors have in fact observed two kinds of difference:

the first in the shape of the decomposition peak: DSC gives a fine exotherm, whose peak width is generally less than 1° C., for insensitive hexogen (I-RDX®), whereas it gives a broad exotherm, whose peak width is generally greater than 5° C., for sensitive or standard hexogen. The term "peak width" means the width at mid height;

the second in the measured decomposition temperature of the sample: the DSC analysis results led for sensitive (standard) hexogen to a decomposition peak maximum at a temperature of 218° C. and for insensitive hexogen to a decomposition peak maximum at a temperature of 226° C. In the present description and in the appended claims, these values of 218° C. and 226° C. should be understood as mean values matched with a standard deviation that is linked to the number of measurements performed on each batch of material. The inventors have thus determined, respectively, a standard deviation of 2.9 (for a temperature of 218° C.) and 1.4 (for a temperature of 226° C.) for a series of 20 measurements. In the case of insensitive hexogen, the decomposition is autocatalytic and is reflected by a rapid rise in the temperature of the sample.

These differences are entirely discriminating and significant for the analysis technique under consideration. They are unexpected.

They demonstrate the value of the present invention. They constitute the basis of said invention.

Thus, according to a first variant, the analysis, performed in the context of the process for determining the sensitive or insensitive nature of a crystalline hexogen, comprises the production and study of a thermogram, more particularly the study of the shape of the decomposition peak:
  fine exotherm for insensitive hexogen;
  broad exotherm for sensitive hexogen (standard);
    and/or of the temperature of the decomposition peak maximum:
    226° C. for insensitive hexogen,
    218° C. for sensitive hexogen (standard).

This first variant is performed in a blind working context, without reference. The exact nature of the hexogen that is subjected to the analysis is obviously not known, but the thermogram of a reference sample is not known either. An "absolute" study of the thermogram of the sample obtained is performed.

According to a second variant, the analysis performed in the context of the process of the invention comprises the production of a thermogram and its comparison with at least one reference thermogram established for a given hexogen of known sensitive or insensitive nature.

This second variant is not performed in a blind working context. It involves a prior analysis on a reference sample. Obviously, said reference sample and said sample to be analyzed are formulated under similar or even identical conditions (nature of the matrix, concentration of hexogen in said matrix, working conditions of the analysis, etc.). The exact nature of the hexogen that is subjected to the analysis is obviously not known, but at least one reference thermogram is available. A "relative" study of the thermogram of the sample obtained is performed.

Whatever the exact working variant, the DSC analysis performed on a novel sample, as described above, makes it possible to obtain the anticipated result: the determination of the sensitive or insensitive nature of the hexogen contained in said sample.

The novel formulation proposed according to the invention for crystalline hexogen makes possible, entirely unexpectedly, via DSC, the discrimination of sensitive hexogen/insensitive hexogen.

According to a second subject, the present invention relates to the formulated hexogen, for the implementation of the process described above; i.e. crystalline hexogen formulated in a matrix consisting essentially of at least one liquid polymer that is suitable for formulating binders for energetic materials charged with nitro organic explosives; and of at least one adsorbent for volatile organic compounds, which is stable at least up to 230° C. and which has low affinity for water.

All the details indicated hereinabove, with reference to the process for determining the sensitive or insensitive nature of a crystalline hexogen, are implicitly reproduced herein, with reference to the second subject of the present invention: the crystalline hexogen formulated in a novel matrix (details regarding the nature of said matrix and regarding the concentration of said hexogen in said matrix).

It is now proposed to illustrate the invention, without limitation in any way, by the attached figure and the example hereinbelow.

FIG. 1 shows the superposition on the same temperature scale of the thermograms obtained by differential scanning calorimetry, performed according to the invention, on a sample of standard hexogen and on a sample of hexogen of I-RDX® type (insensitive hexogen).

EXAMPLE

One particular embodiment of the process (of the invention) for determining the sensitive or insensitive nature of samples is described hereinbelow.

The embodiment described was applied to more than a hundred samples of crystalline hexogens (I-RDX® and standard RDX) and gave reproducible results within an acceptable standard deviation range. Correlations with the characterizations via the DAI method made it possible to validate the results obtained via the process of the present invention.

Hexogen is formulated by simple mixing of the ingredients, used in the following proportions:
RDX: 50 mg±5 mg
liquid polymer: 35 mg±5 mg
adsorbent: 10 mg±2 mg.

The RDX is used in powder form. It was able to be formulated at particle sizes of between less than 3.5 μm and 800 μm.

The liquid polymer is a hydroxytelechelic polybutadiene. Its viscosity is 500 poises at 30° C. The HTPB used is the HTPB R45HTLO sold by the company Sartomer.

The adsorbent is Tenax®-TA, sold by the company Buchem B.V. It is in the form of a powder having the following characteristics:
particle size: 60/80 mesh
specific surface area: 35 m$^2$/g
pore volume: 2.4 cm$^3$/g
mean pore diameter: 200 nm
apparent specific density: 0.25 g/cm$^3$.

The charged matrices obtained are analyzed by DSC under the following conditions:
temperature: from 180 to 240° C.
heating rate: 5° C./minute
capsule: pierced aluminum crucible
gas: under air.

The results obtained via the DSC characterization methods on 20 samples of each batch lead to the values indicated in the table below.

| | Results obtained with the DSC method | | | | |
|---|---|---|---|---|---|
| | Matrix-conditioned product according to the invention | | | Pure product | |
| | Mean T dec. (° C.) (*) | Standard deviation | Energy (mJ) | Mean T dec (° C.) (*) | Standard deviation |
| I-RDX ® | 226.2 | 1.4 | ≈11000 | 235.2 | 1.8 |
| RDX | 218.2 | 2.9 | ≈7000 | 234.6 | 1.2 |

(*) Temperature of the decomposition peak maximum measured on the sample

The sensitive or insensitive nature of each batch was confirmed by means of measurement via the DAI test on explosive compositions formulated with the batches under consideration.

The decomposition of matrix-conditioned I-RDX® according to the invention leads to a fine exothermic peak with a width of less than 1° C., about 0.5° C. under the conditions of the example. The decomposition is autocatalytic and leads under the conditions of the example to a temperature rise of the sample higher than that of nominal heating. The temperature of the sample is then higher than the nominal temperature of the analysis machine. After the decomposition reaction, the sample returns to the nominal temperature. It is common practice to represent the decomposition mode thermogram by relating the measured temperature peak maximum of the sample to the nominal temperature value. It is this representation that is given in FIG. 1 in comparison with the curve measured with standard hexogen in the matrix according to the invention. The width of the decomposition peak measured with standard hexogen is greater than 5° C., about 10° C., under the conditions of the example.

The data contained in the above table and in the attached figure demonstrate the full value of the present invention.

The invention claimed is:

1. A process for determining a sensitive or insensitive nature of a crystalline hexogen, wherein the process comprises:
formulation of said crystalline hexogen in a matrix that consists essentially of:
at least one liquid polymer that is suitable for the formulation of binders for energetic materials charged with nitro organic explosives; and
at least one adsorbent for volatile organic compounds, which is stable at an operating temperature of the analysis and which has low affinity for water,
so as to form a charged matrix with the crystalline hexogen; and
analysis of a sample of said charged matrix by differential scanning calorimetry.

2. The process according to claim 1, wherein said charged matrix contains from 35% to 65% by mass of said crystalline hexogen.

3. The process according to claim 1, wherein said charged matrix contains:
from 35% to 65% by mass of said crystalline hexogen,
from 25% to 50% by mass of said at least one liquid polymer, and
from 5% to 20% by mass of said at least one adsorbent.

4. The process according to claim 1, wherein said at least one liquid polymer is selected from the group consisting of polyethylene glycols, polyoxypropylene glycols, polyesters, and polyethers containing hydroxyl end groups.

5. The process according to claim 1, wherein said at least one liquid polymer is a hydroxytelechelic polybutadiene.

6. The process according to claim 1, wherein said at least one adsorbent is a porous polymer based on a polyphenylene oxide containing 2,6-diphenyl-p-phenylene oxide units.

7. The process according to claim 1, wherein said at least one liquid polymer is a hydroxytelechelic polybutadiene with a molecular mass of between 2000 and 3000 g/mol and said at least one adsorbent is a porous polymer based on a polyphenylene oxide containing 2,6-diphenyl-p-phenylene oxide units with a molecular mass of between 0.5 and $1 \times 10^6$ g/mol.

8. The process according to claim 1, wherein said analysis includes production and study of a thermogram, including study of shapes of decomposition peaks of:
fine exotherm for insensitive hexogen; and
broad exotherm for sensitive hexogen;
and/or of temperatures of decomposition peak maximums of:
226° C. for insensitive hexogen, and
218° C. for sensitive hexogen.

9. The process according to claim 1, wherein said analysis comprises production of a thermogram and its comparison with at least one reference thermogram established for a crystalline hexogen of known sensitive or insensitive nature.

10. A crystalline hexogen formulated in a matrix,
wherein the matrix, into which the crystalline hexogen is charged to form a charged matrix with the crystalline hexogen, consists essentially of:
at least one liquid polymer that is suitable for formulating binders for energetic materials charged with nitro organic explosives; and
at least one adsorbent for volatile organic compounds, which is stable at least up to 230° C. and which has low affinity for water.

11. The hexogen according to claim 10, wherein the charged matrix contains from 35% to 65% by mass of said crystalline hexogen.

12. The hexogen according to claim 10, wherein the charged matrix contains:
from 35% to 65% by mass of said crystalline hexogen,
from 25% to 50% by mass of said at least one liquid polymer, and
from 5% to 20% by mass of said at least one adsorbent.

13. The hexogen according to claim 10, wherein said at least one liquid polymer is selected from the group consisting of polyethylene glycols, polyoxypropylene glycols, polyesters, and polyethers containing hydroxyl end groups.

14. The hexogen according to claim 10, wherein said at least one liquid polymer is a hydroxytelechelic polybutadiene.

15. The hexogen according to claim 10, wherein said at least one adsorbent is a porous polymer based on a polyphenylene oxide containing 2,6-diphenyl-p-phenylene oxide units.

16. The hexogen according to claim 10, wherein said at least one liquid polymer is a hydroxytelechelic polybutadiene with a molecular mass of between 2000 and 3000 g/mol and in which said at least one adsorbent is a porous polymer based on a polyphenylene oxide containing 2,6-diphenyl-p-phenylene oxide units with a molecular mass of between 0.5 and $1 \times 10^6$ g/mol.

17. The process according to claim 1, wherein said charged matrix contains:
from 46% to 59% by mass of said crystalline hexogen,
from 31% to 43% by mass of said at least one liquid polymer, and
from 8% to 14% by mass of said at least one adsorbent.

18. The hexogen according to claim 10, wherein the charged matrix contains:
from 46% to 59% by mass of said crystalline hexogen,
from 31% to 43% by mass of said at least one liquid polymer, and
from 8% to 14% by mass of said at least one adsorbent.

* * * * *